US008795382B2

(12) United States Patent
Lin et al.

(10) Patent No.: US 8,795,382 B2
(45) Date of Patent: *Aug. 5, 2014

(54) CEMENT PRODUCTS AND METHODS OF MAKING AND USING THE SAME

(75) Inventors: Juchui Ray Lin, Bedford, MA (US); Edward S. Ahn, Dover, MA (US); Hansen Yuan, Fayetteville, NY (US); Paul J. Mraz, Duxbury, MA (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/982,461

(22) Filed: Dec. 30, 2010

(65) Prior Publication Data

US 2011/0097420 A1    Apr. 28, 2011

Related U.S. Application Data

(63) Continuation of application No. 11/500,798, filed on Aug. 8, 2006, now Pat. No. 7,947,759.

(60) Provisional application No. 60/706,473, filed on Aug. 8, 2005.

(51) Int. Cl.
*A61F 2/30* (2006.01)
*A61F 2/00* (2006.01)
*A61K 6/083* (2006.01)

(52) U.S. Cl.
USPC ........................................ 623/23.62; 523/115

(58) Field of Classification Search
USPC .................. 623/17.11, 23.48, 23.62; 523/115
See application file for complete search history.

(56) References Cited

U.S. PATENT DOCUMENTS

| | | |
|---|---|---|
| 2,920,971 A | 1/1960 | Stookey |
| 3,107,427 A | 10/1963 | Schmitt et al. |
| 3,117,099 A | 1/1964 | Proops et al. |
| 3,732,087 A | 5/1973 | Grossman |
| 3,981,736 A | 9/1976 | Broemer et al. |
| 4,059,684 A | 11/1977 | Gross et al. |
| 4,239,113 A | 12/1980 | Gross et al. |
| 4,341,691 A | 7/1982 | Anuta |
| 4,554,686 A | 11/1985 | Baker |
| 4,588,664 A | 5/1986 | Fielding et al. |
| 4,643,982 A | 2/1987 | Kasuga et al. |
| 4,652,534 A | 3/1987 | Kasuga |
| 4,775,646 A | 10/1988 | Hench et al. |
| 4,837,279 A | 6/1989 | Arroyo |
| 4,872,936 A | 10/1989 | Engelbrecht |
| 4,910,259 A | 3/1990 | Kindt-Larsen et al. |
| 4,980,404 A | 12/1990 | Aydin et al. |
| 5,204,473 A | 4/1993 | Winter et al. |
| 5,236,458 A | 8/1993 | Ducheyne et al. |
| 5,336,642 A | 8/1994 | Wolcott |
| 5,681,872 A | 10/1997 | Erbe |
| 5,744,001 A | 4/1998 | Linhart et al. |
| 5,824,331 A | 10/1998 | Usala |
| 5,830,492 A | 11/1998 | Usala |
| 5,834,005 A | 11/1998 | Usala |
| 5,914,356 A | 6/1999 | Erbe |
| 5,922,786 A | 7/1999 | Mitra et al. |
| 6,013,591 A | 1/2000 | Ying et al. |
| 6,117,456 A | 9/2000 | Lee et al. |
| 6,126,922 A | 10/2000 | Rozzi et al. |
| 6,133,339 A | 10/2000 | Xie et al. |
| 6,231,881 B1 | 5/2001 | Usala et al. |
| 6,261,587 B1 | 7/2001 | Usala |
| 6,313,192 B1 | 11/2001 | Anstice et al. |
| 6,352,707 B1 | 3/2002 | Usala |
| 6,437,073 B1 | 8/2002 | Gunatillake et al. |
| 6,455,608 B1 | 9/2002 | Jia et al. |
| 6,544,324 B1 | 4/2003 | Lyles et al. |
| 6,752,863 B2 | 6/2004 | Lyles et al. |
| 6,790,877 B2 | 9/2004 | Nakatsuka et al. |
| 6,844,372 B2 | 1/2005 | Goto et al. |
| 6,864,337 B2 | 3/2005 | Yuasa et al. |
| 6,869,984 B2 | 3/2005 | Kawashima et al. |
| 6,906,113 B2 | 6/2005 | Baudin et al. |
| 6,939,900 B2 | 9/2005 | Ario et al. |
| 6,953,594 B2 | 10/2005 | Lee et al. |
| 6,972,130 B1 | 12/2005 | Lee et al. |
| 6,987,136 B2 | 1/2006 | Erbe et al. |

(Continued)

FOREIGN PATENT DOCUMENTS

| | | |
|---|---|---|
| WO | WO 02/13767 A2 | 2/2002 |
| WO | WO 02/13768 A2 | 2/2002 |
| WO | WO 2005/013921 A1 | 2/2005 |

OTHER PUBLICATIONS

American Society for Testing and Materials, "Standard Specification for Acrylic Bone Cement," *Annual Book of ASTM Standards; Medical Devices*, F 451-99a: 56-62 (1999).
3M ESPE, "Z100™ MP Brochure," (1-5) Retrieved from the Internet on Jul. 28, 2005 from www.matweb.com/search/SpecifiedMaterialPrint.asp?bassnum= PMMM02.
Anderson et al., "Semi-Automated Synthesis and Screening of a Large Library of Degradable Cationic Polymers for Gene Delivery," *Angew. Chem. Int. Ed.*, 42: 3153-3158 (2003).
Anderson et al., "A polymer library approach to suicide gene therapy for cancer," *Proceedings of the National Academy of Sciences of the United States of America*, 101(45):16028-16033 (Nov. 1, 2004).
Arote et al., "A biodegradable poly(ester amine) based on polycaprolactone and polyethylenimine as a gene carrier," *Biomaterials*, 28: 735-744 (2007).

(Continued)

*Primary Examiner* — Liam J Heincer
(74) *Attorney, Agent, or Firm* — Leydig, Voit & Mayer, Ltd.

(57) ABSTRACT

Disclosed are cement products, methods of forming cement using the cement product, and methods of using the cement product in orthopedic and dental applications. Generally, the disclosed cement product includes a first component comprising a polymerizable resin comprising ethylenic unsaturated double bond, a second component comprising a compound comprising more than one type of amine selected from the group consisting of primary amines, secondary amines, tertiary amines and quaternary amines, and, optionally, the cement product includes a bioactive component to promote bone formation.

20 Claims, No Drawings

(56) References Cited

U.S. PATENT DOCUMENTS

| | | | |
|---|---|---|---|
| 6,998,447 | B2 | 2/2006 | Irie et al. |
| RE39,196 | E | 7/2006 | Ying et al. |
| 7,132,462 | B2 | 11/2006 | Lehmann et al. |
| 7,275,932 | B2 | 10/2007 | Jin et al. |
| 7,303,814 | B2 | 12/2007 | Lamberti et al. |
| 7,361,216 | B2 | 4/2008 | Kangas et al. |
| 7,368,488 | B2 | 5/2008 | Nishikawa et al. |
| 7,488,762 | B2 | 2/2009 | Takano et al. |
| 7,601,767 | B2 | 10/2009 | Ruppert et al. |
| 7,662,884 | B2 | 2/2010 | Yuasa et al. |
| 7,902,141 | B2 | 3/2011 | Becker et al. |
| 8,029,755 | B2 | 10/2011 | Ahn |
| 8,044,113 | B2 | 10/2011 | Klee |
| 2002/0035169 | A1 | 3/2002 | Nakatsuka et al. |
| 2002/0045678 | A1 | 4/2002 | Lopez et al. |
| 2002/0120033 | A1* | 8/2002 | Jia et al. ............... 523/115 |
| 2002/0161132 | A1 | 10/2002 | Irie et al. |
| 2002/0193547 | A1 | 12/2002 | Yuasa et al. |
| 2003/0083398 | A1 | 5/2003 | Kawashima et al. |
| 2003/0092782 | A1 | 5/2003 | Goto et al. |
| 2003/0134933 | A1 | 7/2003 | Jin et al. |
| 2003/0158288 | A1 | 8/2003 | Lehmann et al. |
| 2003/0215395 | A1 | 11/2003 | Yu et al. |
| 2003/0232746 | A1 | 12/2003 | Lamberti et al. |
| 2003/0232944 | A1* | 12/2003 | Molenberg et al. ............ 528/10 |
| 2004/0059065 | A1 | 3/2004 | Goto et al. |
| 2004/0260011 | A1 | 12/2004 | Yuasa et al. |
| 2005/0031578 | A1 | 2/2005 | Deslauriers et al. |
| 2005/0031704 | A1 | 2/2005 | Ahn |
| 2005/0118230 | A1 | 6/2005 | Hill et al. |
| 2005/0197422 | A1 | 9/2005 | Mayadunne et al. |
| 2005/0238683 | A1 | 10/2005 | Adhikari et al. |
| 2006/0041033 | A1 | 2/2006 | Bisig et al. |
| 2006/0051394 | A1 | 3/2006 | Moore et al. |
| 2006/0216323 | A1 | 9/2006 | Knaack et al. |
| 2006/0247330 | A1 | 11/2006 | Takano et al. |
| 2007/0027285 | A1 | 2/2007 | Gunatillake et al. |
| 2007/0039519 | A1 | 2/2007 | Kangas et al. |
| 2007/0155646 | A1 | 7/2007 | Becker et al. |
| 2007/0173568 | A1 | 7/2007 | Nishikawa et al. |
| 2008/0234404 | A1 | 9/2008 | Klee |
| 2009/0048659 | A1 | 2/2009 | Weber et al. |
| 2009/0169532 | A1 | 7/2009 | Ying et al. |
| 2009/0270527 | A1 | 10/2009 | Lin et al. |

OTHER PUBLICATIONS

Brown, "Solubilities of Phosphates and Other Sparingly Soluble Compounds," *Environmental Phosphorus Handbook*, (Griffith et al., eds.), 203-239 (John Wiley & Sons, Inc. New York, NY, 1973).

Burton et al., "Epoxy Formulations Using Jeffamine® Polyetheramines," *Huntsman Corporation Brochure*, 1-105 (Apr. 27, 2005).

Deramond et al., "Temperature Elevation Caused by Bone Cement Polymerization During Vertebroplasty," *Bone*, 25(2 Supplement): 17S-21S, (Aug. 1999).

European Patent Office, Examination Report in European Patent Application No. 06 800 903.4 (Sep. 17, 2009).

Jagur-Grodzinski et al., "Biomedical application of functional polymers," *Reactive & Functional Polymers*, 39: 99-138 (1999).

Jean et al., "Polyurethane Acrylate/Epoxy-Amine Acrylate Hybrid Polymer Networks," *J. Applied Polymer Science*, 77: 2711-2717 (2000).

Kim et al., "Highly effective and slow-biodegradable network-type cationic gene delivery polymer: Small library-like approach synthesis and characterization," *Biomaterials*, 27: 2292-2301 (2006).

Kincaid, "Epoxy Polyacrylate Hybrids . . . A Continuing Study," *Resolution Performance Products LLC tech paper*, 1-15 (Nov. 2001).

Kokubo et al., "Novel bioactive materials with different mechanical properties," *Biomaterials*, 24(13): 2161-2175 (2003).

Kweon et al., "A novel degradable polycaprolactone networks for tissue engineering," *Biomaterials*, 24: 801-808 (2003).

Lin et al., "Novel Bioreducible Poly(amido amine)s for Highly Efficient Gene Delivery," *Bioconjugate Chemistry*, 18(1): 138-145 (Jan./Feb. 2007).

Lin et al., "Linear poly(amido amine)s with secondary and tertiary amino groups and variable amounts of disulfide linkages: Synthesis and in vitro gene transfer properties," *Journal of Controlled Release*, 116 (2): 130-137 (Nov. 28, 2006).

Liso et al., "Analysis of the Leaching and Toxicity of New Amine Activators for the Curing of Acrylic Bone Cements and Composites," *Biomaterials*, 18(1): 15-20 (Jan. 1997).

Liu et al., "Novel poly(amino ester)s obtained from Michael addition polymerizations of trifunctional amine monomers with diacrylates: safe and efficient DNA carriers," *Chemistry Communication*, (20): 2630-26301 (Oct. 21, 2003).

Liu et al., "Bioactivity and cytocompatibility of zirconia ($ZrO_2$) films fabricated by cathodic arc deposition," *Biomaterials*, 27: 3904-3911 (2006).

Nussbaum et al., "The Chemistry of Acrylic Bone Cements and Implications for Clinical Use in Image-guided Therapy," *J. Vascular and Interventional Radiology.*, 15(2): 121-126 (Feb. 2004).

Pressly, "Complications Related to the Use of Bone Cement and Bone Void Fillers in Treating Compression Fractures of the Spine", *FDA Public Health Web Notification*, 1-3 (May 7, 2004).

Provenzano et al., "Bone Cements: Review of Their Physiochemical and Biochemical Properties in Percutaneous Vertebroplasty," *Am. J. Neuroradiol.*, 25: 1286-1290 (Aug. 2004).

Serbetci et al. "Mechanical and Thermal Properties of Hydroxyapatite-Impregnated Bone Cement," *Turk J. Med. Sci.*, 30: 543-549 (2000).

Srinivasachari et al., "Effects of trehalose click polymer length on pDNA complex stability and delivery efficacy," *Biomaterials*, 28: 2885-2898 (2007).

Zhong et al., "A versatile family of degradable non-viral gene carriers based on hyperbranched poly(ester amine)s," *Journal of Controlled Release*, 109 (1-3): 317-329 (Dec. 5, 2005).

European Patent Office, International Search Report dated Feb. 20, 2007, in PCT/US2006/030764.

Amstutz et al., "The Structure of the Vertebral Spongiosa," *The Journal of Bone and Joint Surgery*, 51B(3): 540-550 (Aug. 1969).

Arrais et al., "Occluding effect of dentifrices on dentinal tubules," *Journal of Dentistry*, 31: 577-584 (2003).

Baroud, A Brief Update on the Biomechanisms Underlying Cement Injection and Leakage in Vertebroplasty, *Supportive Cancer Therapy*, 2(2): 105-108 (Jan. 2005).

Baroud et al., "A new cannula to ease cement injection during vertebroplasty," *Eur. Spine J.*, 14: 474-479 (2005).

Basile et al., "Vertebroplasty in multiple myeloma with osteolysis or fracture of the posterior vertebral wall. Usefulness of a delayed cement injection," *Skeletal Radiol*, 40: 913-919 (2011).

Bastian et al., "Complications related to cement leakage in sacroplasty," *Acta Orthopaedica Belgica*, 7891): 100-105 (2012).

Bohner et al., "Theoretical and experimental model to describe the injection of a polymethylmethacrylate cement into a porous structure," *Biomaterials*, 24: 2721-2730 (2003).

Georgy, "Feasibility, Safety and Cement Leakage in Vertebroplasty of Osteoporotic and Malignant Compression Fractures Using Ultra-Viscous Cement and Hydraulic Delivery System," *Pain Physician*, 15: 223-228 (May/Jun. 2012).

Kubinek et al., "Examination of dentin surface using AFM and SEM," *Modern Research and Educational Topics in Microscopy*, (Eds. Méndez-Vilas and Diaz), 593-598 (2007).

La Maida et al., "Cement leakage: safety of minimally invasive surgical techniques in the treatment of multiple myeloma vertebral lesions," *Eur. Spine J.*, 21(Suppl. 1): S61-S68 (2012).

Liu et al., "Filling in dentinal tubules," *Nanotechnology*, 18: 1-6 (2007).

Nieuwenhuijse et al., "Cement leakage in percutaneous vertebroplasty for osteoporotic vertebral compression fractures: identification of risk factors," *The Spine Journal*, 1-10 (2011).

Ørstavik, "Materials used for root canal obturation: Technical, biological and clinical testing," *Endodontic Topics*, 12: 25-38 (2005).

Parfitt et al., "Bone Histomorphometry: Standardization of Nomenclature, Symbols, and Units, Report of the ASBMR Histomorphometry Nomenclature Committee," *Journal of Bone and Mineral Research*, 2(6): 595-610 (1987).

(56) References Cited

OTHER PUBLICATIONS

Sharma et al., "Nanocharacterization in Dentistry," *Int. J. Mol. Sci.*, 11: 2523-2545 (2010).

Wegrzyn et al., "Role of Trabecular Microarchitecture and Its Heterogeneity Parameters in the Mechanical Behavior of Ex Vivo Human $L_3$ Vertebrae," *Journal of Bone and Mineral Research*, 25(11): 2324-2331 (Nov. 2010).

* cited by examiner

CEMENT PRODUCTS AND METHODS OF MAKING AND USING THE SAME

CROSS-REFERENCE TO RELATED APPLICATIONS

This patent application is a continuation of copending U.S. patent application Ser. No. 11/500,798 filed on Aug. 8, 2006, now U.S. Pat. No. 7,947,759, which claims the benefit of U.S. Provisional Patent Application No. 60/706,473 filed on Aug. 8, 2005, the disclosures of which are incorporated by reference herein in their entirety.

BACKGROUND OF THE INVENTION

The demand for restorative cement products useful in orthopedic and dental treatments has been increasing, in part, as a consequence of lengthening lifespans and a steadily larger pool of candidates for orthopedic and dental treatments. A second factor driving demand is the increasing tendency among individuals to maintain or adopt a more active lifestyle as they age. This trend makes procedures that use restorative cement products more beneficial and more desirable. A third factor driving the demand for restorative cement products is the development of new techniques that use such cement products.

Among the most widely used cement products in orthopedic and dental systems are those based on the polymerizable acrylate resin polymethylmethacrylate (PMMA). PMMA cements are typically prepared from two components: a liquid and a powder. The liquid includes methylmethacrylate (MMA) monomers, an accelerator, and/or an inhibitor. The powder includes PMMA microspheres, a polymerization initiator, and/or a radio-opacifier. This system has been in procedures that polymerize the cement in situ, i.e., at the site of injury being treated. For example, PMMA cements have been used in orthopedic implant surgery to bond the implant to bone.

However, some concern has been expressed that the exothermic polymerization of PMMA in situ can lead to thermal necrosis. For example, it has been reported that previously studied bone cement products produce a maximum rise in temperature ranging from 80° C. to 124° C. Serbetci et al., "Mechanical and Thermal Properties of Hydroxyapatite-Impregnated Bone Cement," *Turk. J. Med. Sci.*, 30: 543-549 (2000). These temperatures exceed the limits for avoiding thermal tissue damage and, thus, have led to concern regarding the heat generated by bone cement polymerization in situ.

PMMA cements have also been used to treat bone damage in patients with osteoporosis. According to the National Osteoporosis Foundation, about 700,000 vertebral fractures occur annually; approximately 270,000 of these fractures are painful and clinically diagnosed. While most patients are treated non-operatively, those that do not respond to conservative treatment can be left with persistent pain and limited mobility. These patients are potential candidates for vertebroplasty or kyphoplasty procedures: two minimally invasive procedures that use PMMA to treat vertebral compression fractures. However during vertebroplasty or kyphoplasty, leakage of liquid from low viscosity PMMA bone cements can result in "soft tissue damage as well as nerve root pain and compression. Other reported complications generally associated with the use of bone cements in the spine include pulmonary embolism, respiratory and cardiac failure, abdominal intrusions/ileus, and death. Each of these types of complications has been reported in conjunction with the use of these products in both vertebroplasty and kyphoplasty procedures." 2004 FDA Public Health Web Notification "Complications Related to the Use of Bone Cement in Treating Compression Fractures of the Spine" (issued by Laura Alonge, Office of Surveillance and Biometrics).

Additionally, unreacted components of PMMA cements have been identified as a potential source of toxicity in the body. Thus, besides, toxicity due to thermal necrosis, studies have suggested that certain PMMA cement products can produce toxicity due to leaching of unconsumed MMA monomers and/or the polymerization activator. Liso et al., "Analysis of the Leaching and Toxicity of New Amine Activators for Curing of Acrylic Bone Cements and Composites", *Biomaterials* 18: 15-20 (1997).

The need for new restorative cement products that address the aforementioned concerns is widely recognized in the field.

BRIEF SUMMARY OF THE INVENTION

The invention provides a cement product that includes a first component and a second component. The first component comprises a polymerizable resin that includes an ethylenic unsaturated double bond. The second component includes a compound that includes more than one type of amine selected from the group consisting of a primary amine, a secondary amine, a tertiary amine, or a quaternary amine. The cement product can also, optionally, include an additional filler such as an inert filler or a bioactive component that promotes bone growth. In some embodiments, the cement product further comprises a third component including an oxygen-containing ring structure that is capable of reacting in a polymerization reaction with the first component, the second component or both. In other embodiments, the first component further comprises an oxygen-containing ring structure that is capable of reacting in a polymerization reaction with the first component, second component, or both. In preferred embodiments, the first component comprises at least one ethylenic unsaturated double bond and an epoxide, such as a glycidyl group. In preferred embodiments, the second component includes a polyalkyleneimine, such as polyethyleneimine (PEI) or a derivative thereof.

The invention also provides a method of forming cement, the method comprising mixing the first component of the cement product with the second component of the cement product to thereby form cement. The invention further provides a method of treating a patient in need of treatment for a bone defect, wherein the method includes forming cement according to the method of invention and delivering the cement to the defective bone as part of a procedure for repairing the bone defect.

The invention is based, in part, on the discovery that the polymerizable resin of the first component can be combined with the amine-containing compound of the second component in a polymerizing cement-hardening reaction that produces only a mild increase in temperature or no increase in temperature at all. Consequently, even when the product is delivered to the site of restoration and cement-hardening polymerization reactions proceeds in situ, the cement product can be used with less (or without any) concern for thermal necrosis.

The invention is also based, in part, on the discovery that the cement product can be formulated so that, when the components of the cement product are mixed, the resulting cement is injectable. In other words, the first, second, and optional third components can be formulated to produce a cement mix that has the appropriate flowability and viscosity properties for an injectable cement. Moreover, the improved flowability and viscosity of the mixture can secure more homogeneous dispersion and mixing of the components upon delivery of the cement. The disclosed first, second, and optional third components can also be formulated so that when combined, the components react to form a crosslinked thermoset network that is ultimately not soluble and not fusible and consume nearly all monomers and oligomers thus reducing the amount of unreacted starting material or by-products that can leach from the formed cement. Additionally, the amine-containing compound of the second component in the cement product can, in certain embodiments, reduce or eliminate the need for a leachable free radical polymerization initiator and/or a chemical accelerator such as those used in the thermoplastic PMMA bone cement products. Thus, the aforementioned advantages can reduce the risks of chemical tissue damage associated with the cement product disclosed herein.

DETAILED DESCRIPTION OF THE INVENTION

The cement product of the present invention includes at least a first and a second component. The first component includes a polymerizable resin. The second component includes a compound comprising more than one type of amine selected from the group consisting of a primary amine, a secondary amine, a tertiary amine, or a quaternary amine. The cement products of the present invention can further comprise a compound comprising an oxygen-containing ring. The cement products of the present invention can also further comprise a filler such as an inert filler or a bioactive component that promotes bone growth. Each component of the cement product can also, optionally, include additional materials.

The first component of the cement product includes one or more biocompatible polymerizable resins selected from a wide array of compositions. Polymerizable groups can be polymerized by Michael addition reactions, by cations such as carbocations, by ion radicals or combinations thereof. Preferred polymerizable resins include one or more ethylenically unsaturated polymerizable group.

Polymerizable resins suitable for the first component include acrylic resins. Suitable acrylic resins include methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate ("HEMA"), hydroxypropyl acrylate, hydroxypropyl methacrylate, tetrahydrofurfuryl acrylate, tetrahydrofurfuryl methacrylate, glycerol mono- and di-acrylate, glycerol mono- and dimethacrylate, ethyleneglycol diacrylate, ethyleneglycol dimethacrylate, polyethyleneglycol diacrylate where the number of repeating ethylene oxide units vary from 2 to 30, polyethyleneglycol dimethacrylate where the number of repeating ethylene oxide units vary from 2 to 30, especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanediol diacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexamethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'-bis(4-acryloxyphenyl)propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, 2,2'-bis[3 (4-phenoxy)-2-hydroxypropane-1-acrylate]propane, propoxylated (2) neopentylglycol diacrylate (Sartomer SR9003), isobornyl methacrylate (Sartomer SR423), aromatic acrylate oligomer (Sartomer CN137), aliphatic allyl oligomer (Sartomer CN9101), dimethylaminoethyl methacrylate (DMAEMA), methylene bisacrylamide (MBA), dimethylaminopropylmethacrylamide, methacrylamido-propyltrimethylammonium chloride and the like. All products designated herein by reference to "Sartomer" and product number are available from Sartomer Company, Inc. (Exton, Pa.).

Other polymerizable resins that can be used in the first component include acrylamide, methylene bis-acrylamide, methylene bis-methacrylamide, diacetone/acrylamide diacetone methacrylamide, N-alkyl acrylamides and N-alkyl methacrylamides where alkyl is a lower hydrocarbyl unit. Other suitable examples of polymerizable resins can include polymerizable groups selected from isopropenyl oxazoline, vinyl azalactone, vinyl pyrrolidone, styrene, divinylbenzene, urethane acrylates, urethane methacrylates, polyol acrylates, and polyol methacrylates.

In certain embodiments, the first component can include polylactic acid (D and L), polyglycolic acid, polylactic/polyglycolic acid copolymers, vinyl group containing polyesters such as polypropylenefumarate and polypropyleneitaconate, polydioxane, poly($\epsilon$-caprolactone), poly (valerolactone), poly(trimethylene carbonate), poly (tyrosine-carbonates) and poly(tyrosine-acrylates), poly (imino carbonates), poly(hydroxybutyrate) (PHB), poly (hydroxyvalerate), poly(tartonic acid), poly($\beta$-malonic acid), polyhydroxycarboxylic acids, polybutyrene succinate, polybutylene adipate, aliphatic diisocyanate based polyurethanes, peptide-based polyurethanes, polyester or polyorthoester based polyurethanes, polyphosphazenes incorporating amino acid ester, glucosyl, glyceyl, lactate or imidazolyl side groups, collagen, chitosan, alginate, cellulose, starches, sugars, polypeptides, polyethylene glycol, vinyl pyrrollidones, acrylamides and methacrylates or any of their derivates or copolymers, or a copolymer micelle such as the triblock copolymer PEO-PPO-PEO, PPO-PEO-PPO, polyvinylpyridine-polystyrene-polyvinylpyridine (PVP-PS-PVP), PS-PVP-PS, PS-PEO-PS, PEO-PS-PEO. In certain preferred embodiments, the first component comprises a resorbable material that is flowable at room temperature comprising polymerizable functional groups, such as vinyl group containing polyesters such as polypropylenefumarate and polypropyleneitaconate.

Preferred polymerizable resins for use in the first component include a Michael addition polymerizable or a cationically (e.g., carbocationically) polymerizable group and an oxygen-containing ring. Thus, preferred polymerizable resins include epoxides, oxetanes, oxolanes, $C_3$-$C_8$ cyclic acetals, $C_3$-$C_{12}$ lactams, $C_3$-$C_{12}$ lactones, and $C_5$-$C_{20}$ spiro-cyclic compounds that contain oxygen atoms in their rings.

Particularly preferred polymerizable resins for the first component include epoxy resins, which feature an oxygen-containing epoxide ring. Exemplary epoxy resins are epoxy acrylates or methacrylates. Epoxy resins can include monomeric epoxides, polymeric epoxides, and combinations thereof. Epoxy resins can be aliphatic, cycloaliphatic, aromatic or heterocyclic. Polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendant epoxy groups (e.g., a glycidyl methacrylate polymer or copolymer). Epoxides can be pure compounds or may be mixtures containing one, two, or more epoxy groups per molecule. The "average" number of epoxy groups per molecule is determined by dividing the total number of epoxy groups in epoxy-containing material by the total number of epoxy molecules present. Epoxides used in the first compound can have, for example, an average of at least 1 polymerizable epoxy group per molecule, and preferably an average of at least about 1.5 polymerizable epoxy groups, and more preferably an average of at least about 2 polymerizable epoxy groups.

Accordingly, preferred polymerizable resins for the first component include ethoxylated trimethylolpropane triacrylate, epoxy acrylate, modified epoxy acrylate (e.g., Sartomer CN115), bisphenol A epoxy methacrylate oligomer (Sartomer CN-151), aliphatic acrylate modifier (Sartomer MCURE 201 and Sartomer MCURE400), glycidyl acrylate of bis-phenol A and the diglycidyl methacrylate of bis-phenol A (bis-GMA). Useful epoxy-containing materials also include those which contain cyclohexene oxide groups such as the epoxycyclohexanecarboxylates, typified by 3,4-epoxy-cyclohexylmethyl-3,4-epoxycyclohexanecarboxylate, 3,4-epoxy-2-methylcyclohexylmethyl-3,4-epoxy-2-methylcy-clohexane carboxylate, and bis(3,4-epoxy-6-methylcyclohexylmethyl)adipate. For a more detailed list of useful epoxides of this nature, see U.S. Pat. No. 3,117,099, incorporated herein by reference.

More preferred polymerizable resins for the first component feature an oxygen containing ring (e.g., an epoxide) and an acrylate moiety (e.g., acrylate, methacrylate) that are covalently linked and in close proximity to each other as depicted in the structure of Formula 1.

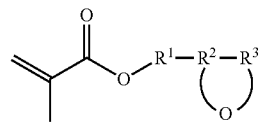

Formula 1

For example, in the structure of Formula 1, the acrylate and the oxygen containing ring structure are separated by the covalent linkage group $R^1$. $R^1$ can be a $C_6$-$C_{20}$ aromatic group, a $C_1$-$C_{20}$ aliphatic group, a $C_3$-$C_{16}$ cyclic group, a polymeric group, or a dendritic group. In addition, $R^1$ can contain one or more polymerizable groups such as epoxides and other suitable oxygen containing rings, ethylenic unsaturated double bonds, and the like. Preferably $R^1$ is any group that does not interpose more than 1, 2, 3, 4 or 5 atoms in the shortest covalent linkage between the acrylate and the oxygen containing ring structure. $R^2$ and $R^3$ represent any substituents capable of forming oxygen containing ring structures. Typically $R^2$ and $R^3$ are each independently selected from CR'R", C=O, O(C=O), NR', and O, wherein R' and R" are each independently selected from the group consisting of H, $C_1$-$C_{12}$-alkyl, $C_3$-$C_{10}$-cycloalkyl, Cl, Br, and OH. When $R^1$, $R^2$ and $R^3$ are each $CH_2$, the structure of Formula 1 represents glycidyl methacrylate (GMA) polymerizable resin.

The polymerizable resin of the first component can include one or more materials that vary from low molecular weight monomeric materials to high molecular weight polymers. The polymers may vary greatly in the nature of their backbone and substituent groups. For example, the backbone may be of any type and substituent groups thereon can be any group that does not substantially interfere with radical or cationic curing at room temperature or body temperature. Permissible substituent groups can include halogens, ester groups, ethers, sulfonate groups, siloxane groups, nitro groups, phosphate groups, and the like. The molecular weight of the epoxy-containing materials can vary from about 20 daltons to about 100,000 daltons, preferably from about 140 daltons to about 30,000 daltons.

The polymerizable resin of the first component can be copolymerized with additional acrylates. For example, when the first component includes an epoxide resin such as GMA, the cement product may also include a second polymerizable resin for copolymerization. Such co-polymerizable resins include methyl methacrylate, ethyl methacrylate, propyl methacrylate, and higher methacrylates, acrylates, ethacrylates, and similar species. Other types of copolymerizable material include epoxide compounds, polyurethane-precursor species, and a wide host of other materials. Still other examples of copolymerizable monomers that can be used in the cement product include methyl-, ethyl, isopropyl-, tert-butyloctyl-, dodecyl-, cyclohexyl-, chlorolethyl-, tetrachloroethyl-, perfluorooctyl-hydroxyethyl-, hydroxypropyl-, hydroxybutyl-, 3-hydroxyphenyl-, 4-hydroxyphenyl-, aminoethyl-, aminophenyl-, and thiophenyl-, acrylate, methacrylate, ethacrylate, propacrylate, butacrylate and chloromethacrylate, as well as the homologous mono- and di-acrylic acid esters of bisphenol-A, dihydroxydiphenyl sulfone, dihydroxydiphenyl ether, dihydroxybiphenyl, dihydroxydiphenyl sulfoxide, and 2,2-bis(4-hydroxy-2,3,5,6-tetrafluorophenyl)propane. Additional copolymerizable monomers capable of sustaining a polymerization reaction include di-, tri-, and higher ethylene glycol acrylates such as ethylene glycol dimethacrylate, diethylene glycol dimethacrylate, trimethylene glycol dimethacrylate, trimethylol propane trimethacrylate, and the like. In some cases, mixtures of two, three, and more polymerizable species can be combined to good effect.

The second component of the cement product includes a compound comprising more than one type of amine selected from the group consisting of a primary amine, a secondary amine, a tertiary amine, and a quaternary amine. Suitable compounds for the second component include aliphatic polyamines, aromatic polyamines, or mixtures of both. Polyamines that can be used in the second component include phenylenediamine, ethylenediamine, triethylenetetramine, and a wide variety of other aliphatic and aromatic diamines that polymerize when mixed with the polymerizable resin of the first component. Suitable compounds for the second component include modified polyamino acids such as polylysines and imidazole-modified polylysines. Suitable polyamines can include branched dendrimers with multiple types of amines, such as polyamidoamine (PAMAM) dendrimers.

Preferred amine-containing compounds of the second component include polyalkyleneamines and derivatives thereof such as polyethyleneimine (PEI) and PEI derivatives, polypropyleneimine (PPI) and PPI derivatives, which typically include primary, secondary and tertiary amines. The PEI or PEI derivative can also include quaternary amines. PEI derivatives include ethoxylated PEI, hydroxyethoxylated PEI, and hydroxypropylated PEI. The PEI or PEI derivatives can be branched or linear. Preferably the PEI or the PEI derivative has a sufficiently low molecular weight that it is a liquid. For example, the PEI or PEI derivative can have an average molecular weight of less than 200 kDa, less than 150 kDA, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 10 kDa, less than 5 kDa or less than 2 kDa. Preferably the PEI or PEI derivative has an average molecular weight of less than 1 kDa and greater than 0.4 kDa.

Optionally, any one of the embodiments of the cement products disclosed herein can further include a third component comprising a compound comprising an oxygen-containing ring. The oxygen-containing ring can be any suitable oxygen-containing ring, for example, any oxygen containing ring described herein. Typically the oxygen-containing ring is selected from epoxides, oxetanes, oxolanes, $C_3$-$C_8$ cyclic acetals, $C_3$-$C_{12}$ lactams, $C_3$-$C_{12}$ lactones, and $C_5$-$C_{20}$ spirocyclic compounds that contain oxygen atoms in their rings.

Desirably the ratio of equivalents of acceptor hydrogen to equivalents of donor hydrogen is from about 0.5:1 to about 1:0.5, preferably 0.75:1 to about 1:0.75, more preferably 0.9:1 to about 1:0.9, and most preferably about 1:1. The equivalents of acceptor hydrogen is the average molecular weight of all compounds in the first and optional third components comprising polymerizable groups (e.g., ethylenic double bond groups, oxygen-containing ring groups) divided by the total number of acceptor hydrogen groups. The equivalents of donor hydrogen can be calculated as the average molecular weight of all compounds comprising amine groups (in the second component) divided by the total number of donor hydrogen groups. For example, the "donor" hydrogen equivalent weight in the amine functionality of PEI is 43 Da while the "acceptor" ethylenic unsaturated double bond or oxygen containing ring on GMA monomer (molecular weight is 142 Da), the equivalent weight of each acceptor functionality is 72 Da.

Optionally, any one of the embodiments of the cement products disclosed herein can further include mixing a filler with the additional first, second, and optional third component of the cement product. The filler can be inert, or alternatively the filler can be comprised by the bioactive component described herein. Inert fillers include glass fillers, such as, CORTOSS™ from OrthoVita (Malvern, Pa.) that have good strength characteristics. Bioactive components are useful for promoting bone tissue growth around the restorative cement and, preferably, bone tissue ingrowth into the cement. In addition, the bioactive component can serve as a stiffening and strengthening agent for the cement product. Representative documents describing such materials include U.S. Pat. Nos. 2,920,971, 3,732,087, 3,981,736, 4,652,534, 4,643,982, 4,775,646, 5,236,458, 5,336,642, 5,681,872, and 5,914,356, as well as Brown, W. F., "Solubilities of Phosphate & Other Sparingly Soluble Compounds," in *Environmental Phosphorous Handbook*, Ch. 10 (1973). All of the foregoing patents and reference documents are incorporated herein by reference.

Typically the bioactive component includes a bioactive glass ceramics, Bioglass™ (sold by NovaBone), Cervital™, water-soluble glasses, collagen, grafted bone material such as allografts, autografts, and xenografts, calcium phosphate ceramics, or any other bioactive material known to promote bone tissue formation. The bioactive component can include known bioactive materials such as densified and microporous hydroxyapatite, fluorapatite, oxyapatite, wollastonite, apatite/wollastonite glass ceramics, anorthite, calcium fluoride, calcium sulfate, agrellite, devitrite, canasite, phlogopite, monetite, brushite, octocalcium phosphate, whitlockite, cordierite, berlinite, combeite, tetracalcium phosphate, tricalcium phosphate (TCP) (e.g., α- and β-tricalcium phosphates), amorphous calcium phosphate, dicalcium phosphate, phosphoric acid crystals, disodium hydrogen phosphate, and other phosphate salt-based bioceramics. Preferably the bioactive components are particles that are fully dense having no internal microporosity, a particle size of 0.5 microns or more and 100 microns or less (e.g., 80 microns or less, 50 microns or less, or 30 microns or less), and a surface area of 50 $m^2$/g or less, 25 $m^2$/g or less, 10 $m^2$/g or less, 5 $m^2$/g or less, or 2.5 $m^2$/g or less. The particle size distribution can be broad, bimodal, or preferably trimodal, also of which being less than about 500 micrometers, with less than 10% by weight being sub 0.5 microns sized.

In some embodiments, the bioactive component is surface modified with one or more coupling groups. Suitable coupling groups include, for example, alkoxysilanes containing epoxide, amine, or vinyl groups, organic isocyanates, acrylic acids, methacrylic acids, polyacrylic acids, citric acids, zirconates, titanates, diamines, amino acids, and polypeptides.

In other further embodiments, the filler can include biological and/or pharmaceutical agents to enhance and accelerate bone formation such as BMP's, bisphosphonates, gene delivery vectors (promoting osteogenesis or preventing osteolysis), stem cells (stem cell can engineered by gene delivery vectors to upregulate expression of desired proteins such as BMP's), antibiotics, pain killers, etc. The biological additive can be any suitable biological additive, for example plasmid DNA or RNA or proteins (e.g., bone morphogenetic proteins 2, 4, 7). The pharmaceutical additive can be any suitable pharmaceutical additive, for example bisphosphonates (e.g., alendronate) and cis-platinum, antibiotics, anti-inflammatories, anti-arthritism, erythropoeitin, and the like.

The amount of filler added can represent from about 10 to about 95% by weight of total cement mix. For example, preferably an inert filler represents from about 65% to about 85% by weight of total cement mix. Preferred densified microcrystalline and nanocrystalline bioactive hydroxyapatite, tricalcium phosphate, and bioceramic content can range from about 10 to about 99% by weight, preferably less than 85% by weight, or more preferably from about 50-80% by weight of that filler.

Preferably, the bioactive component includes a nanocrystalline and/or poorly crystalline apatite material, such as hydroxyapatite or another apatitic calcium phosphate. Nanocrystalline and/or poorly crystalline apatite materials have been described, for example, in U.S. Pat. Nos. 6,117,456, 6,953,594, 6,013,591 (which has been reissued as U.S. Reissue No. RE 39,196), and U.S. Pat. No. 6,972,130. The foregoing patent documents are incorporated herein by reference. Nanocrystalline apatite material is also commercially available, for example, from Angstrom Medica (Woburn, Mass.). In certain embodiments, the bioactive component includes nanocrystalline hydroxyapatite (nHA) whisker crystals. These nHA crystals can form a fibrous network throughout the polymerized cement that reinforces the cement under compressive loads.

Batches of nHA whisker can be synthesized in reactors by feeding 0.167 M solution of reagent grade $Ca(NO_3)_2.4H_2O$ (CaN) (Fluka Chemie AG, Buchs, Switzerland) onto a well-mixed solution of 0.100 M $(NH_4)_2HPO_4$ (NHP) (Fluka) and aging for 100 hours. Production of nHA whisker can be optimized by controlling temperature and concentration of starting materials. Optimal production occurs at temperatures of about 25° C. to about 200° C., more preferably about 60° C. to about 120° C., and even more preferably about 80° C. to about 100° C., which allows the growth of anisotropic nHA crystals having multiple different aspect ratios that are greater than 1. For example, batches of nHA crystals can have aspect ratios (length:diameter) ranging from about 1.5:1 to about 1000:1, from about 2:1 to about 500:1, from about 3:1 to about 250:1, from about 4:1 to about 200:1, from about 5:1 to about 150:1, from about 6:1 to about 125:1, from about 7:1 to about 100:1, from about 8:1 to about 75:1, from about 9:1 to about 60:1, or from about 10:1 to about 50:1. Generally, production temperatures should not exceed the boiling point of the reaction mix. Reactant concentration can also be controlled by adjusting temperature, i.e., by raising the temperature to remove water and thereby increase reactant concentration. For example, the reaction can be optimized by comparing the nHA produced in a reaction after 5% water removal, 10% water removal, and 15% water removal. The particle size of these batches can be determined using laser diffraction. Surface area and porosity measurements are obtained using nitrogen gas adsorption. Particle settling data can also be obtained. Whisker crystal size and morphology of the hydroxyapatite are confirmed using transmission electron microscopy.

Following chemical precipitation and aging, the powders can be recovered by centrifugation and washed with aqueous solvent to remove residual ionic species. Subsequently, these powders can undergo a second series of washes with organic solvent to remove any remaining precipitation solvent. After removing residual solvent, the resulting precipitate can be re-suspended in an organic monomer, oligomer, or prepolymer solution to prevent hard agglomeration or alignment of whisker particles and, thereby, produce a highly dispersed suspension of nHA whiskers that can be used in the bioactive component of the cement product described herein.

The nHA whiskers of a bioactive component can also be sheared into agglomerated bundles of highly aligned whiskers of different particle size, particle density, and porosity. The nHA powder recovered by centrifugation can be washed as described above, except that instead of the final resuspension in solvent, the excess organic solvent can be removed from the powder, and shear forces applied to allow nHA whiskers to align. Shear forces for this secondary processing technique can be applied using a centrifuge, a pigment mixer and a planetary ball mill.

These two processing (non-sheared and sheared) preparations can produce nHA whiskers having different in particle size, surface area, and porosity, all of which will influence handling and volume loading in the polymer system, as well as the properties of the final cement product that includes such nHA whiskers. Thus, the properties of nHA whiskers can be optimized so that when mixed with the first and the second component of a cement product disclosed herein, the resulting cement has the viscosity and flowability characteristics that are appropriate for the application in which the cement is to be used. For example, the properties of nHA whiskers can be optimized for use in different injectable embodiments of the cement product of the invention.

The first, second, and optional third component described herein and, optionally, the filler described herein can all be selected to provide a thermosetting cement product that is mildly exothermic, is isothermic, or is mildly endothermic. Therefore, the cement product disclosed herein can be used to treat bone defects with less concern for thermal necrosis than is associated with the more exothermic restorative cements that are currently available. It has been reported that thermal necrosis of bone tissue can occur when temperatures surpass 50° C. for more than one minute. Provenzano et al., "Bone Cements: Review of Their Physiochemical and Biochemical Properties in Percutaneous Vertebroplasty," *Am J. Neuroradiol.* 25: 1286-1290 (2004). Thus, preferably, the first component, the second component, and, optionally, the bioactive component are selected so that when the components are mixed to form a bone cement, the polymerization (i.e., cement hardening) reaction does not rise in temperature or, alternatively, produces a mild rise in temperature that is insufficient to heat the surrounding tissue to a temperature that exceeds 50° C. for more than one minute.

In certain embodiments of the cement product disclosed herein, the first component, the second component, and optionally, the third component and/or the filler are selected so that when the components and, optionally, the filler are mixed, the resulting polymerization and crosslinking reaction produces a rise in temperature that does not exceed 50° C., 49° C., 48° C., 47° C., 46° C., 45° C., 44° C., 43° C., 42° C., 41° C., 40° C., 39° C., 38° C., 37° C., or 36° C. for a period of one minute. In certain more preferred embodiments of the cement product disclosed herein, the first component, the second component and, optionally, the third component and/or the filler are selected so that when they are mixed, the resulting polymerization reaction produces a rise in temperature that does not exceed 35° C., 34° C., 33° C., 32° C., 31° C., 30° C., 29° C., 28° C., 27° C., 26° C., 25° C., 24° C., 23° C., 22° C., 21° C., 20° C. for a period of one minute. In certain still more preferred embodiments of the cement product disclosed herein, the first component, the second component and, optionally, the third component and/or the filler are selected so that when the components are mixed, the resulting polymerization reaction produces a rise in temperature that does not exceed 19° C., 18° C., 17° C., 16° C., 15° C., 14° C., 13° C., 12° C., 11° C., 10° C. for a period of one minute. In certain most preferred embodiments of the cement product disclosed herein, the first component, the second component and, optionally, the third component and/or the filler are selected so that when the components are mixed, the resulting polymerization reaction produces a rise in temperature that does not exceed 9° C., 8° C., 7° C., 6° C., 5° C., 4° C., 3° C., 2° C., 1° C., 0° C. for a period of one minute. The rise in temperature can be measured at room temperature (about 25°

C.) or at body temperature (about 37° C.). The rise in temperature can be measured according to techniques described in, for example, "Standard Specification for Acrylic Bone Cement" ASTM F 451-99 from ASTM International (West Conshohocken, Pa.), Serbetci et al., "Mechanical and Thermal Properties of Hydroxyapatite-Impregnated Bone Cement," 30: 543-549 (2000) and Deramond et al., "Temperature Elevation Caused by Bone Cement Polymerization during Vertebroplasty," *Bone* S25:S17-S21 (1999).

The following theoretical considerations may be useful in the selection of a first, second, and optional third component that, when mixed, have optimally low exothermic profile. Without desiring to be bound by theory, it is believed that the components disclosed herein each includes material with multiple functional groups that, when mixed, participate in multiple endothermic and/or isothermic reactions that consume at least some of the energy generated by exothermic polymerizing reactions. In other words, the polymerization reactions of exothermic function groups are used at the molecular level to initiate endothermic or isothermic reactions of different reactive groups. This tandem sequence of exothermic and endothermic/isothermic reactions can be optimized by matching the characteristic thermal zone of the exothermic function groups with that of the endothermic/isothermic function groups, thereby reducing or eliminating the global temperature increase of the polymerization reaction. For example, mixing the first component and the second component can produce (i) mildly exothermic ring-opening reactions with the amino groups of the second component as well as (ii) carbocationic, onium formation, and/or Michael additions, which are endothermic or adiabatic.

The first and second components and, optionally the third component and/or the filler described herein can all be selected to provide a thermosetting cement product that is suitable for injection. The first, second, optional third component and optional filler can be selected to provide the viscosity and flowability characteristics that are appropriate for the application in which the cement is to be used. Relatively low viscosity, syringable pastes are suited for filling bony defects, fracture repairs, and implant fixations and revisions. Syringable pastes should flow to fill voids, and crevices, and adhere tightly to the surface of the bone, tissue, or implant. Preferably, a syringable paste has a viscosity suitable for injection through a 4-18 gauge needle, e.g., a 6-12 gauge needle. Flowability can be important for tight adherence and removal of micromotion when implant securing is being achieved. The lack of implant motion can reduce inflammation and determine the success of the implant system over time. Higher viscosity pastes are desirable for larger, load bearing bone defects and easily accessible fracture sites. A "putty" can be manipulated, sculpted and cured in place with immediate high strength capability. Oncological bony defects are well-suited for highly loaded, highly bioactive composites. The use of hand mixed pastes of the first and second component can also facilitate the addition of medicaments, antibiotics, or bone growth factors, e.g., prior to injecting or otherwise applying the pastes.

In certain embodiments of the cement product, the first, second, and optional third components described herein and, optionally, the filler are selected so that, when mixed, they form a cement having a desirable setting time and/or desirable mechanical strength. Desirable setting times vary according to the cement's intended application. Desirable setting times can include from about 1 to about 30 minutes (again depending on the application). For certain injectable applications desirable setting times can range from about 2 to about 25 minutes, from about 3 to about 20 minutes, or from about 5 to about 15 minutes.

Desirable mechanical strength will also vary according to the cement's intended applications. Moreover, the type and amount of filler can greatly influence one more type of mechanical strength. Desirable mechanical strength properties include the following. The compressive strength typically is from about 50 MPa to about 250 MPa. Generally, compressive strength increases with the amount of filler included. When the cement does not include a filler, the compressive strength typically is from about 50 MPa to about 100 MPa. When the cement includes a filler, the compressive strength typically is from about 100 MPa to about 250 MPa. Preferably the compressive strength is about 50 MPa or more, about 100 MPa or more, or about 150 MPa or more. A preferred tensile strength is from about 10 to about 100 MPa (e.g., about 20 MPa or more, about 40 MPa or more, or about 60 MPa or more). A preferred shear strength is from about 30 MPa to about 150 MPa (e.g., about 50 MPa or more, about 80 MPa or more, or about 110 MPa or more). A preferred flexural strength is from about 20 MPa to about 100 MPa (e.g., about 30 MPa or more, about 40 MPa or more, or about 50 MPa or more). A preferred infinite compression fatigue is from about 20 MPa to about 150 MPa (e.g., about 40 MPa or more, about 70 MPa or more, or about 100 MPa or more). A preferred tensile fatigue is from about 5 MPa to about 40 MPa (e.g., about 10 MPa or more, about 20 MPa or more, or about 30 MPa or more). The compression modulus typically is in the range of about 20 MPa to about 5 GPa, preferably in the range of about 50 MPa to about 2 GPa. And most preferred in range of about 100 MPa to about 1 GPa. The deformation percentage ranges from about 10% to about 90%, preferably from about 20% to about 80% and most preferably from about 30% to about 50%.

The different types of mechanical strengths can be measured according to tests known in the art, such as ASTM F451 (Standard Specification for Acrylic Bone Cement), ASTM D695 (Test method for compressive properties of rigid plastics), and ASTM C-773 (Standard Test Method for Compressive (Crushing) Strength of Fired Whiteware Materials). ASTM tests are published by ASTM International (West Conshohocken, Pa.).

The cement product of the invention can be packaged such that the first, second, and optional third components are not mixed until ready to use. For example, the first, second, and optional third components can each be packaged in a separate container. Alternatively, the first, second, and optional third components can each be packaged in a separate chamber of the same container, e.g., a dual chambered self-mixing syringe. More generally, syringes and other devices adapted for injecting cement formed from the first, second, and third components described herein are known in the art. The bioactive component can, optionally, be packaged with the first component only, with the second component only, with the third component if present, separately from each of the first, second and optional third components, or divided between two or more components.

In some embodiments, the cement product of the invention can be used without chemical additives such as an initiator, a catalyst, and/or a stabilizer. In other embodiments the cement product can include significantly smaller amounts of such additives. These embodiments can be used to decrease the risk of chemical necrosis associated with the product.

In other embodiments, the cement product of the invention further includes one or more additives, such as, an initiator, a catalyst, and/or a stabilizer, to optimize the working and setting times of the cement product. Such additives, which are known in the art of restorative cements, include heat curing catalyst and photoinitiators. For example, the cement product of the invention can further include a quinone photoinitiator in an amount ranging from about 0.01% to about 10% by weight of the compound of the second component. More preferably, the quinone is present in an amount of about 0.1% to about 5% by weight of the compound of the second component. Preferred quinone photoninitiators include alpha diketone(quinones). A more preferred quinone photoinitiator is camphoroquinone. Other photoinitiator systems include a 2-benzyl-2-(dimethylamino)-4'-morpholino-butyrophenone, or mixtures of 2-hydroxyethyl-2-methyl-1-phenyl-1-propanone and diphenyl (2,4,6-trimethylbenzyl) phosphine oxide. In certain embodiments, the cement product can include the appropriate relative amounts of (i) butylated hydroxytoluene (BHT) stabilizer, (ii) benzoyl peroxide (BPO) catalyst, and (iii) the compound of the second component, wherein the appropriate relative amounts are selected to optimize working time and setting time.

The first, second, and optional third components can also be selected so that when combined, the components react to form a crosslinked thermoset network that is ultimately not soluble and not fusible and consume nearly all monomers and oligomers thus reducing the amount of unreacted starting material or by-products that can leach from the formed cement. For example, in preferred embodiments, at least 80%, 85%, or 90% of reactants are converted to into the polymer network. More preferably, 95%, 96%, 97%, 98%, 99%, or 100% of reactants are converted. Additionally, the amine-containing compound of the second component in the cement product can, in certain embodiments, reduce or eliminate the need for a leachable free radical polymerization initiator and/or a chemical accelerator such as those used in the thermoplastic PMMA bone cement products. Thus, the aforementioned advantages can reduce the risks of chemical tissue damage associated with the cement product disclosed herein.

In another aspect, the invention provides a method of forming cement. The method includes providing the first component and the second component of the cement product described herein and mixing the two components to thereby form cement. Optionally, the method can further include combining the bioactive component of the cement product described herein.

As described above for the cement product, the method of forming cement disclosed herein includes preferred embodiments of the first component, second component and optional bioactive component. Preferred embodiments of the first component for use in the method include an epoxy resin, while more preferred embodiments of the first component include both an epoxide and a glycidyl ether group as shown in Formula 1. Even more preferred embodiments of the first component include GMA and bis-GMA. More preferred embodiments of the second component for use in the method include PEI or a derivative thereof. In the most preferred method of forming cement, the first component includes GMA or bis-GMA or ethoxylated bisphenol A di(meth)acrylate and the second component includes PEI, PEI doped with 0.1-5% by weight of camphorquinone, or a derivative thereof.

The invention also provides a method of treating a patient in need of treatment for a bone defect. The method of treatment generally includes forming cement according to the method of forming cement described herein and then delivering the cement to the defective bone in the patient as part of a procedure for repairing the bone defect. Bone defects that can be treated using the method include defects due to osteoporosis, stress fracture, traumatic fracture, compression fracture, and combinations thereof. For example, the method of treatment described herein can be used to treat patients with a vertebral bone defect due to trauma or osteoporosis. The treatment can include using the cement product disclosed herein to form cement that is injected to the vertebra, for example, as part of a vertebroplasty or kyphoplasty procedure to stabilize the vertebra.

The bone cement product and methods described herein can also be used in dental procedures that require the use of restorative cement.

The following examples further illustrate bone cement products and methods of forming cement according to the invention but, of course, should not be construed as in any way limiting its scope.

EXAMPLE 1

The following describes the preparation of an acrylic resin-based paste-paste restorative cement product that includes a nano-hydroxyapatite bioactive component according to the invention. The cement product includes two parts. Part A is described in Table 1 and includes the polymerizable resin of the first component. Part B is described in Table 2 and includes the polyamine of the second component. Parts A and B were each formulated as a non-dripping paste-like shear thinning cream. The bioactive component was divided between Parts A and B.

TABLE 1

|  | (parts by weight) |
| --- | --- |
| Glycidyl dimethacrylate (GMA) (Sartomer SR379) | 58.74 |
| Ethoxylated trimethylolpropanetriacrylate (Sartomer SR9035) | 5.30 |
| NanoHydroxyapatite (Angstrom Medica, Inc.) | 35.96 |

TABLE 2

|  | (parts by weight) |
| --- | --- |
| Polyethyleneimine (PEI) (Aldrich, Cat No.: 408719) | 55.0 |
| NanoHydroxyapatite (Angstrom Medica, Inc.) | 45.0 |

Both Part A and Part B had fast and excellent dispersion, they were highly formable, shapeable and easily delivered by a syringe delivery system. A cement product with a 4 to 1 ratio (by weight) of Part A to Part B was mixed on a watch glass pre-cooled to refrigerator temperature (0-5° C.). The cement mix was used to fill a ¼" i.d. hollow tubule to a height of 4 inches within 10 minutes. The filled tubule was placed into a 37° C. incubator. The cement mix was dried to touch after 5 to 10 minutes in the oven. The mix had no observable exotherm as determined by a thermocouple per ASTM F451-99.

The formed cement was released from the molding tubule and kept in the incubator oven for 3 days. The cement was compression tested with a MTI 10K compression tester (Measurements Technology, Inc., Roswell, Ga.) using a crosshead displacement rate of 1 mm/min. The specimen was tested according to ASTM C773 (ASTM International (West Conshohocken, Pa.)) (Procedure B) using test population 4 and compression modulus average 82.25 MPa. Maximum force average was 820 N, while the average peak stress was 21.32 MPa, and average strain 28.31%.

The foregoing example demonstrates that the cement product of the invention can be used in a method of forming cement that is injectable and has no observable rise in temperature.

EXAMPLE 2

The following describes the preparation of another acrylic resin-based paste-paste restorative cement product with a bioactive component according to the invention. The bioactive component includes both nano-hydroxyapatite and nano-hydroxyapatite whiskers ranging in size from 5-10 nm in diameter to 250 nm in length. The cement product includes two parts. Part A is described in Table 3 and includes the polymerizable resin of the first component. Part B is described in Table 4 and includes the polyamine of the second component. Parts A and B were each formulated as a non-dripping paste-like shear thinning cream. The bioactive component was divided between Parts A and B.

TABLE 3

|  | (parts by weight) |
|---|---|
| Glycidyl dimethacrylate (GMA) (Sartomer SR379) | 69.10 |
| Ethoxylated trimethylolpropanetriacrylate (Sartomer SR9035) | 3.78 |
| NanoHydroxyapatite whiskers (Angstrom Medica, Inc.) | 12.40 |
| NanoHydroxyapatite (Angstrom Medica, Inc.) | 14.72 |

TABLE 4

|  | (parts by weight) |
|---|---|
| PEI (Polyethyleneimine, Aldrich Cat No.: 408719) | 55.0 |
| NanoHydroxyapatite (Angstrom Medica, Inc.) | 45.0 |

Both Parts A and Part B had fast and excellent dispersion, were highly formable, shapeable, and easily delivered by a syringe delivery system. A cement product with a 5.3 to 1 ratio (by weight) of Part A to Part 13 was mixed on a watch glass pre-cooled to refrigerator temperature (0-5° C.). The cement mix was used to fill a ¼" i.d. hollow tubule to a height of 4 inches within 10 minutes. The filled tubule was placed into a 37° C. incubator. The cement mix was dried to touch within 15 minutes in the oven. The mix had no observable exotherm as determined by a thermocouple per ASTM F451-99.

The formed cement was released from the molding tubule and kept in the incubator oven for 3 days. The cement was compression tested with a MTI 10K compression tester (Measurements Technology, Inc., Roswell, Ga.) using a crosshead displacement rate of 1 mm/min. The specimen was tested according to ASTM C773 (ASTM International) (Procedure B) using test population 3 and compression modulus average 29.45 MPa. Maximum force average was 284 N, while the average peak stress was 7.38 MPa, and average strain was 30.14%.

The foregoing example demonstrates another embodiment of the cement product of the invention that can be used in a method of forming cement that is injectable and has no observable rise in temperature.

EXAMPLE 3

The following describes the preparation of an acrylic resin-based paste-paste restorative cement product with a bioactive component that includes nano-hydroxyapatite whiskers ranging in size from 5-10 nm in diameter to 250 nm in length. The cement product includes two parts. Part A is described in Table 5 and includes the polymerizable resin of the first component. Part B is described in Table 6 and includes the polyamine of the second component. Parts A and B were each formulated as a non-dripping paste-like shear thinning cream. The bioactive component was divided between Parts A and B.

TABLE 5

|  | (parts by weight) |
|---|---|
| Glycidyl dimethacrylate (GMA) (Sartomer SR379) | 70.0 |
| NanoHydroxyapatite whiskers (Angstrom Medica, Inc.) | 30.0 |

TABLE 6

|  | (parts by weight) |
|---|---|
| PEI (Polyethyleneimine, Aldrich Cat No.: 408719) | 52.37 |
| NanoHydroxyapatite whiskers (Angstrom Medica, Inc) | 47.63 |

Both Parts A and Part B had fast and excellent dispersion, were highly formable, shapeable, and easily delivered by a syringe delivery system. A cement product with a 4 to 3 ratio (by weight) of Part A to Part B was mixed on a watch glass pre-cooled to refrigerator temperature (0-5° C.). The cement mix was used to fill a ¼" i.d. hollow tubule to a height of 1.25 inches within 15 minutes. The filled tubule was placed in a 37° C. incubator. The cement mix was dried to touch within 15 minutes in the oven. The mix had no observable exotherm as determined by a thermocouple per ASTM F451-99.

The formed cement was released from the molding tubule and kept in the incubator oven for 2 days. The cement was compression tested with a MTI 10K compression tester (Measurements Technology, Inc., Roswell, Ga.) using a crosshead displacement rate of 1 min/min. The specimen was tested according to ASTM C773 (ASTM International) (Procedure B) using test population 1 and compression modulus average 47.4 MPa. Maximum force average was 626.8 N, while the average peak stress was 16.3 MPa, and average strain was 47.2%.

The foregoing example demonstrates another embodiment of the cement product of the invention that can be used in a method of forming cement that is injectable and has no observable rise in temperature.

EXAMPLE 4

18.9631 grams of ethoxylated trimethylolpropanetriacrylate (SR9035, Sartomer) was added to 1.0380 grams of glycidyl methacrylate (SR379, Sartomer) to make the first component of the cement product. The first component was vertexed and mixed into a single phase. The second component of 0.3974 grams of polyethyleneimine (PEI, Aldrich, cat. no. 408719) was mixed with 2.7643 grams of the first component on a watch glass pre-cooled to 0-5° C. The mix was stirred at ambient temperature. The viscose fluid was transferred to a ¼" i.d. latex tubule with capped.ends (3" long). The tubule was placed in a 37° C. incubator oven. The cement dried to touch within 15 minutes. The cement rod was released after 5 days and the released rod was in the incubator oven for an additional 7 days. The cement was compression tested with a MTI 10K compression tester (Measurements Technology, Inc., Roswell, Ga.) using a crosshead displacement rate of 1 mm/min. The specimen was tested according to ASTM C773 (ASTM International) (Procedure B) using test population 1 and compression modulus average 13.56 MPa. Maximum force average was 58.82 N, while the average peak stress was 2.08 MPa, and average strain was 16%.

The foregoing example demonstrates another embodiment of the cement product of the invention can be used in a method of forming cement that is injectable.

EXAMPLE 5

A two component cement product was mixed to form cement. The first component comprising 0.7143 grams of glycidyl methacrylate (SR379, Sartomer) was added to the second component comprising 0.4713 grams of polyethyleneimine (PEI, Aldrich, cat. no. 408719). A white viscose fluid formed immediately with no temperature raise. The fluid was stirred well at ambient temperature and transferred to a i.d. latex tubule with capped.ends (3" long). The tubule was placed in a 37° C. incubator oven. The cement dried to touch within 15 minutes. The cement rod was released after 5 days and the released rod was in the incubator oven for an additional 7 days. The cement rod was compression tested with a MTI 10K compression tester (Measurements Technology, Inc., Roswell, Ga.) using a crosshead displacement rate of 1 mm/min. The specimen was tested according to ASTM C773 (ASTM International) (Procedure B) using test population 1 and compression modulus average 13.56 MPa. Maximum force average was 58.82 N, while the average peak stress was 2.08 MPa, and average strain was 16%.

The foregoing example demonstrates another embodiment of the cement product of the invention that can be used in a method of forming cement that is injectable.

EXAMPLE 6

This example compares the exothermic profile of various embodiments of the cement product according to the invention, each embodiment having different relative amounts of the first and second component.

The relative amounts of the first component, comprising GMA, and the second component, comprising PEI, were varied as indicated in Table 7. Table 7 also indicates (a) predicted millimoles of double bonds (C=C) in the glycidyl groups of the GMA (assuming 100% purity and GMA monomeric molecular weight of 142.15 daltons), (b) millimoles of PEI repeat units (assuming 100% purity and repeat unit molecular weight of 43.07 daltons), (c) equivalent ratio of GMA glycidyl groups to PEI repeat units, (d) the observed temperature rise after mixing for two minutes, and (e) setting time in a 37° C. incubator oven after $N_2$ gas purging.

TABLE 7

|  | Cement Product | | | | | |
| --- | --- | --- | --- | --- | --- | --- |
|  | 6-A | 6-B | 6-C | 6-D | 6-E | 6-F |
| GMA (grams) | 0.7169 | 1.4287 | 1.1222 | 0.6841 | 0.6425 | 0.7361 |
| Glycidyl (C=C) mmole | 5 | 10.05 | 7.89 | 4.8 | 4.5 | 5.17 |
| PEI (grams) | 0.4387 | 0.6770 | 0.4307 | 0.5444 | 0.6066 | 0.7356 |
| PEI mmole | 10.18 | 15.7 | 10.00 | 12.64 | 14.08 | 17.08 |
| GMA:PEI mmole ratio | 0.49:1 | 0.64:1 | 0.79:1 | 0.38:1 | 0.32:1 | 0.30:1 |

TABLE 7-continued

|  | Cement Product | | | | | |
| --- | --- | --- | --- | --- | --- | --- |
|  | 6-A | 6-B | 6-C | 6-D | 6-E | 6-F |
| Temperature rise (° C.) | 27-29 | 27-29 | 27-28 | 27-29 | 25-28 | 25-28 |
| Set time (min.) | 35 | 135 | 135 | 35 | 38 | 35 |

The results in Table 7 indicate that when GMA is in excess, the polymer system is more sluggish in curing. On the other hand, when the stoichiometric ratio of reacting functional groups are equal, or when PEI is in excess, more rapid curing is achieved.

The results are consistent with the following polymerization model. When PEI equivalents are in excess, Michael addition reactions (of C=C double bonds and the primary and secondary amine groups in the PEI) are dominant and there is less dampening of exothermic temperature rise, since there are not enough endothermic reactions available to compensate for the exothermic glycidyl-amine reaction. When excess PEI is reduced and there are nearly equal amounts of PEI repeat equivalents as C=C double bond equivalents, or when there is a slight molar excess of C=C double bond groups (e.g., a slight excess of GMA) the system can begin to favor the endothermic reactions that dampen the exothermic temperature rise. This model suggests that adding a vinyl or allyl component in addition to the first GMA component can supply additional double bonds, which are used not only for Michael addition to amines on PEI but also for carbocation reaction sites. In other words, vinyl oligomers such as (bis-GMA) or other vinyl oligomers described herein may be added as an additional polymerizable resin to the first and second components of the cement product. It should be noted, however, that too much excess GMA can result in a slower set time.

EXAMPLE 7

The following describes the preparation of another acrylic resin-based paste-paste restorative cement product with a bioactive component according to the invention. The bioactive component includes Spectrum Chemicals poorly crystallized calcium phosphate tribasic (Catalog #C1155) dense powder. The cement product includes two parts. Part A is described in Table 8 and includes the polymerizable resin of the first component. Part B is described in Table 9 and includes the polyamine of the second component. Parts A and B were each formulated as a non-dripping paste-like thick ointment. The bioactive component was divided between Parts A and B.

TABLE 8

|  | (parts by weight) |
| --- | --- |
| Ethoxylated(2) Bisphenol A Diacrylate (SPP M-193) | 58.48 |
| Calcium Phosphate Tribasic (Spectrum Chemical C1155) | 41.52 |

TABLE 9

| | (parts by weight) |
|---|---|
| PEI (Polyethyleneimine, Aldrich Cat No.: 408719) | 42.44 |
| Calcium Phosphate Tribasic (Spectrum Chemical C1155) | 57.56 |

Both Parts A and Part B were thick ointment-like pastes. A cement product with a 2.1 to 1 ratio (by weight) of Part A to Part B was mixed on a watch glass. The cement mix was used to fill a ¼" i.d. hollow tubule to a height of 6 inches within 3 minutes. The cement mix was dried to touch within 3 minutes at room temperature. The mix had exotherm temperature raise of 6 deg C./min as determined by thermocouple per ASTM F451-99.

The formed cement was released from the molding tubule and kept at room temperature for 16 days. The cement was compression tested with a MTI 10K compression tester (Measurements Technology, Inc., Roswell, Ga.) using a crosshead displacement rate of 10 mm/min. The specimen was tested according to ASTM C773 (ASTM International) (Procedure B) using test population 3 and compression modulus average 176 MPa. Maximum force average was 1357 N, while the average peak stress was 40.8 MPa and average strain was 30.72%.

EXAMPLE 8

The following describes the preparation of another acrylic resin-based paste-paste restorative cement product without a bioactive component according to the invention. The neat polymeric resin product includes part A and part B as described in Table 10. Parts A and B were each formulated as a liquid resin.

TABLE 10

| | (parts by weight) |
|---|---|
| A: Ethoxylated(2) Bisphenol A Diacrylate (SPP M-193) | 82.9 |
| B: PEI (Polyethyleneimine, Aldrich Cat No.: 408719) | 17.1 |

Both Parts A and Part B were free flowing low viscosity liquid. A thermoset product with a 4.85 to 1 ratio (by weight) and 1 to 1 by mole of Part A to Part B was mixed on a watch glass. The cement mix was used to fill a ¼" i.d. hollow tubule to a height of 6 inches within 5 minutes. The cement mix was dried to touch within 15 minutes in an incubator oven. The mix had little exotherm temperature rise as determined by thermocouple per ASTM F451-99.

The formed thermoset solid tube was released from the molding tubule and kept in the incubator oven for 14 days. The thermoset was compression tested with a MTI 10K compression tester (Measurements Technology, Inc., Roswell, Ga.) using a crosshead displacement rate of 10 mm/min. The specimen was tested according to ASTM 0773 (ASTM International) (Procedure B) using test population 5 and compression modulus average 30 MPa. Maximum force average was 2376 N, while the average peak stress was 75 MPa and average strain was 50.28%. The solid tube is compressible and recovered to its original length after the stress was released.

EXAMPLE 9

The following describes the preparation of another acrylic resin-based paste-paste restorative cement product without a bioactive component according to the invention. The neat polymeric resin product includes part A and part B as described in Table 11. Parts A and B were each formulated as a liquid resin.

TABLE 11

| | (parts by weight) |
|---|---|
| A: Ethoxylated(2) Bisphenol A Diacrylate (SPP M-193) | 75.85 |
| B: PEI (Polyethyleneimine, Aldrich Cat No.: 408719) | 24.15 |

Both Parts A and Part B were free flowing low viscosity liquid. A thermoset product with a 3 to 1 ratio (by weight) and 1 to 1.6 by mole of Part A to Part B was mixed on a watch glass. The cement mix was used to fill a ¼" i.d. hollow tubule to a height of 6 inches within 8 minutes. The cement mix was dried to touch within 25 minutes in an incubator oven. The mix had little exotherm temperature rise as determined by a thermocouple per ASTM F451-99.

The formed thermoset solid tube was released from the molding tubule and kept in the incubator oven for 14 days. The thermoset was compression tested with a MTI 10K compression tester (Measurements Technology, Inc., Roswell, Ga.) using a crosshead displacement rate of 10 mm/min. The specimen was tested according to ASTM C773 (ASTM International) (Procedure B) using test population 5 and compression modulus average 76.53 MPa. Maximum force average was 650 N, while the average peak stress was 20.33 MPa and average strain was 50.91%. The solid tube is compressible and recovered to its original length after stress was released.

EXAMPLE 10

The following describes the preparation of another acrylic resin-based paste-paste restorative cement product without a bioactive component according to the invention. The neat polymeric resin product includes two parts. Part A and part B are described in Table 10. Parts A and B were each formulated as a liquid resin.

TABLE 12

| | (parts by weight) |
|---|---|
| A: BisGMA (Sartomer CN151) | 85.66 |
| B: PEI (Polyethyleneimine, Aldrich Cat No.: 408719) | 14.34 |

Parts A is a sticky high viscosity fluid and was heated to 37 C to lower its viscosity and Part B is a free flowing low viscosity liquid. A thermoset product with a 4 to 1 ratio (by weight) and 1 to 1 by mole of Part A to Part B was mixed on a watch glass The cement mix was used to fill a ¼" i.d. hollow tubule to a height of 8 inches within 20 minutes. The thermoset mix was sticky and the hollow tubule was end-capped with a stop-cork plug then it was placed in a 37 C incubator oven. The mix had little exotherm temperature rise as determined by thermocouple per ASTM F451-99.

It was harden overnight. The formed thermoset solid tube was kept in the incubator oven for 10 days. Then the hollow tubule was removed. The thermoset was compression tested with a MTI 10K compression tester (Measurements Technology, Inc., Roswell, Ga.) using a crosshead displacement rate of 10 mm/min. The specimen was tested according to ASTM C773 (ASTM International) (Procedure B) using test population 4 and maximum compression modulus was 434 MPa. Maximum force was 4287 N, while the maximum peak stress was 111 MPa, and maximum strain was 70%. The solid tube is compressible and recovered to its original length after stress was released.

The foregoing example demonstrates that the cement product of the invention can be used in a method of forming cement that is injectable and is only mildly exothermic. The foregoing example also indicates that the ratio of first and second components in the cement product of the invention can be adjusted to further reduce the exothermic rise in temperature produced by mixing the components of the cement product.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a bone defect, the method comprising:
    injecting a first component comprising a biocompatible polymerizable resin that includes one or more ethylenically unsaturated polymerizable groups selected from the group consisting of mono-, di-, and multi-ethylenic unsaturated double bonds, wherein the resin includes an epoxide;
    injecting a second component comprising a compound that includes more than one type of amine selected from the group consisting of a primary amine, a secondary amine, a tertiary amine, and a quaternary amine;
    injecting a bioactive component filler, wherein the bioactive component is (a) injected with the first component or with the second component, (b) injected separately from each of the first and second components, or (c) divided between the first and second components and is injected with the first and second components;
    mixing the first component, the second component, and the bioactive component together, wherein the first and second component react with each other in a polymerization reaction, and thereby forming an orthopedic cement; and
    delivering the orthopedic cement to the site of a bone defect in a patient in need of treatment for the bone defect.

2. The method of claim 1, the method further comprising injecting a third component that includes an oxygen-containing ring structure; and
    including the third component in the mixing and polymerization a polymerization reaction, wherein the bioactive component is (a) injected with the first component, the second component, or with the third component, (b) injected separately from each of the first, second and third components, or (c) is divided between two or more of the first, second and third components and is injected with the two or more other components.

3. The method of claim 1, the method comprising polymerizing the first and second components in a reaction produces a maximum sustained temperature rise of less than 30° C. for one minute, according to the method described in ASTM F 451-99.

4. The method of claim 1 wherein the cement has a setting time of 1 to 30 minutes at 37° C. after mixing.

5. The method of claim 1, wherein the resin includes a multifunctional alkoxylated (meth)acrylate with either aromatic or aliphatic ether linkages.

6. The method of claim 1, wherein the resin includes epoxy acrylate, modified epoxy acrylate, bisphenol A epoxy methacrylate oligomer, or a combination thereof.

7. The method of claim 1, wherein the bioactive component comprises a material selected from the group consisting of hydroxyapatite, α-tricalcium phosphate, β-tricalcium phosphate, and combinations thereof.

8. The method of claim 7, wherein the bioactive component material comprises fully dense particles having a particle size of between 0.5 microns and 100 microns.

9. The method of claim 1, wherein:
    the bone defect is a vertebral defect; and
    the cement is delivered to a vertebra during vertebroplasty or kyphoplasty.

10. The method of claim 9, wherein the first component and the second component are injected from separate chambers of a dual-chambered device and the bioactive component is divided between the first and second component.

11. A method of treating a bone defect, the method comprising:
    injecting a first component comprising a biocompatible polymerizable resin that includes one or more ethylenically unsaturated polymerizable groups selected from the group consisting of mono-, di-, and multi-ethylenic unsaturated double bonds;
    injecting a second component comprising a compound that includes more than one type of amine selected from the group consisting of a primary amine, a secondary amine, a tertiary amine, and a quaternary amine;
    injecting a bioactive component filler, wherein the bioactive component is (a) injected with the first component or with the second component, (b) injected separately from each of the first and second components, or (c)

divided between the first and second components and is injected with the first and second components;

injecting a photoinitiator;

mixing the first component, the second component, the bioactive component, and the photoinitiator together, wherein the first and second component react with each other in a polymerization reaction, and thereby forming an orthopedic cement; and delivering the orthopedic cement to the site of a bone defect in a patient in need of treatment for the bone defect.

12. The method of claim 11, the method further comprising injecting a third component that includes an oxygen-containing ring structure; and including the third component in the mixing and polymerization a polymerization reaction, wherein the bioactive component is (a) injected with the first component, the second component, or with the third component, (b) injected separately from each of the first, second and third components, or (c) is divided between two or more of the first, second and third components and is injected with the two or more other components.

13. The method of claim 11, the method comprising polymerizing the first and second components in a reaction produces a maximum sustained temperature rise of less than 30° C. for one minute, according to the method described in ASTM F 451-99.

14. The method of claim 11 wherein the cement has a setting time of 1 to 30 minutes at 37° C. after mixing.

15. The method of claim 11, wherein the resin includes a multifunctional alkoxylated (meth)acrylate with either aromatic or aliphatic ether linkages.

16. The method of claim 11, wherein the resin includes ethoxylated trimethylolpropane triacrylate, epoxy acrylate, modified epoxy acrylate, bisphenol A epoxy methacrylate oligomer, glycidyl acrylate of bis-phenol A, diglycidyl methacrylate of bisphenol A (bis-GMA), or a combination thereof.

17. The method of claim 11, wherein the bioactive component comprises a material selected from the group consisting of hydroxyapatite, $\alpha$-tricalcium phosphate, $\beta$-tricalcium phosphate, and combinations thereof.

18. The method of claim 11, wherein the bioactive component material comprises fully dense particles having a particle size of between 0.5 microns and 100 microns.

19. The method of claim 11, wherein:

the bone defect is a vertebral defect; and the cement is delivered to a vertebra during vertebroplasty or kyphoplasty.

20. The method of claim 11, wherein the first component and the second component are injected from separate chambers of a dual-chambered device and the bioactive component is divided between the first and second component.

* * * * *